United States Patent
Miguel (12)

(10) Patent No.: US 6,551,265 B1
(45) Date of Patent: Apr. 22, 2003

(54) ADVANCING ANTISEPTIC MARKING PEN

(76) Inventor: Harry San Miguel, 260 McDonald Ave., San Jose, CA (US) 95116

( * ) Notice: Subject to any disclaimer, the term of this patent is extended or adjusted under 35 U.S.C. 154(b) by 0 days.

(21) Appl. No.: 10/074,457

(22) Filed: Feb. 11, 2002

(51) Int. Cl.[7] ............................................... A61M 35/00
(52) U.S. Cl. ............................................. 604/1; 401/57
(58) Field of Search ................................. 604/310, 309, 604/1, 2, 116, 187, 192; 401/63, 55; 206/535

(56) References Cited

U.S. PATENT DOCUMENTS 3,708,235 A * 1/1973 Kolomeir ..................... 401/57
4,854,761 A * 8/1989 Smith et al. ................. 401/196

* cited by examiner

Primary Examiner—Dennis Ruhl
Assistant Examiner—Linh Truong
(74) Attorney, Agent, or Firm—The Kline Law Firm

(57) ABSTRACT

An advancing antiseptic marking pen in which a barrel of the pen holds a plurality of antiseptic/marking tips. The tips contain a colored antiseptic substance. When an indicated area on the patient's body is cleansed, the area remains marked by the antiseptic/colorant fluid chosen so that the user of the pen can clearly ascertain the indicated area. A protective cap fits over the open end of the pen to prevent bacteria and other contaminants from contaminating the antiseptic/marking tips. When the pen is to be used, the operator must of course first remove the protective cap. The operator then depresses and slides an advancing tab on a top side of the barrel of the pen to advance an antiseptic/marking tip to an in-use position. After the indicated area is highlighted, cleansed, and simultaneously marked, the operator again depresses and slides the advancing tab to eject the used tip. The protective cap is then replaced by the operator so that the pen can be conveniently stored in a pocket. Ejection of a used tip does not automatically expose a new tip. Unused tips remain below the opening of the pen until the tips are advanced by again operating the advancing tab. This process further protects against contamination of the antiseptic/marking tips.

12 Claims, 6 Drawing Sheets

ADVANCING ANTISEPTIC MARKING PEN

BACKGROUND OF THE INVENTION

1. Field of the Invention

The present invention relates generally to medical equipment. The invention is an antiseptic marking pen which will enable medical personnel after using the device to eject a used antiseptic/marking tip and introduce in its place a clean uncontaminated replacement by depressing and sliding an advancement tab on the pen.

2. Description of the Prior Art

When medical personnel administer an injection to a patient, draw blood, or perform any intravenous procedure, the area of the skin to be pierced must first be cleansed. The antiseptic used is most often isopropyl alcohol, in part due to its rapid drying characteristic. The rapid drying time can also be a drawback however, as isopropyl alcohol is colorless, and therefore invisible when it has dried, leaving the person performing the procedure in some doubt as to the exact location of the cleansed area. A common procedure among some phlebotomists, for example, is to make a mark on the skin with a pen to identify a desired point of entry after the area is cleansed with isopropyl alcohol. While quick and convenient, this procedure is clearly not optimal, as the pen is very likely to be a source of contamination.

The prior art includes several references for devices that enable the user to either mark or cleanse the site of an intended skin puncture. One such reference for a marking device is the "Hypodermic Syringe and a Method for Marking Injections" by Carswell, U.S. Pat. No. 5,192,270, issued Mar. 9, 1993. This reference discloses a cover for the syringe that has a marking pigment installed at the closed end of the cover. One drawback to this device is that the exposed pigment will not only mark the injection site, but also the user's pocket. Further, there is no provision for an antiseptic agent.

A reference that discloses an antiseptic means integral to the syringe unit is the "Needle Cover Assembly having Self-Contained Drug Applicator" of Chiappetta, U.S. Pat. No. 5,989,229, issued Nov. 23, 1999. This device utilizes a drug swab contained in a cover for the needle of the syringe.

There is no reference in the prior art that discloses a device that enables the user to both cleanse and to mark the intended site of an injection or other sub-dermal procedure. This means that the medical technician must use more than one instrument for each such procedure.

Accordingly, it is an object of the present invention to provide a device that can both apply an antiseptic while simultaneously marking a site on a patient's skin.

It is a further object of the present invention to provide a device that accomplishes sterile marking.

It is a still further object of the present invention to provide a device that is quick and easy to use.

SUMMARY OF THE INVENTION

The present invention is an advancing antiseptic marking pen. A barrel of the pen holds a plurality of antiseptic/marking tips. The tips contain a colored antiseptic substance. Products such as BETADINE® or a chlorhexadine isopropyl alcohol colorant combination work quite well due to their antiseptic capability and bright coloring. When an indicated area on the patient's body is cleansed, the area remains marked by the antiseptic colorant combination so that the user of the pen can clearly ascertain the indicated area. A protective cap fits over the open end of the pen to prevent bacteria and other contaminants from contacting the antiseptic/marking tips.

When the pen is to be used, the operator must of course first remove the protective cap. The operator then depresses and slides an advancing tab on a top side of the barrel of the pen to advance an antiseptic/marking tip to an in-use position. After the indicated area is cleansed (and simultaneously marked), the operator again depresses and slides the advancing tab to eject the used tip. The protective cap is then replaced by the operator so that the pen can be conveniently stored in a pocket, and so that the antiseptic/marking tips remain in an airtight environment.

An advantage of the present invention is that the operator can use a single instrument to cleanse and mark an indicated area.

Another advantage of the present invention is that the pen is easy to use with one hand.

A still further advantage of the present invention is that after use, the antiseptic/marking tips are simply discarded by pressing and sliding the advancing tab, thereby eliminating cleanup time and effort. When all the antiseptic/marking tips are used, the pen itself may be discarded so that no refilling of the device is required. Alternatively, refill cartridges of the antiseptic/marking tips can be used with the device.

These and other objects and advantages of the present invention will become apparent to those skilled in the art in view of the description of the best presently known mode of carrying out the invention as described herein and as illustrated in the drawings.

DETAILED DESCRIPTION OF THE INVENTION

Figure 1:
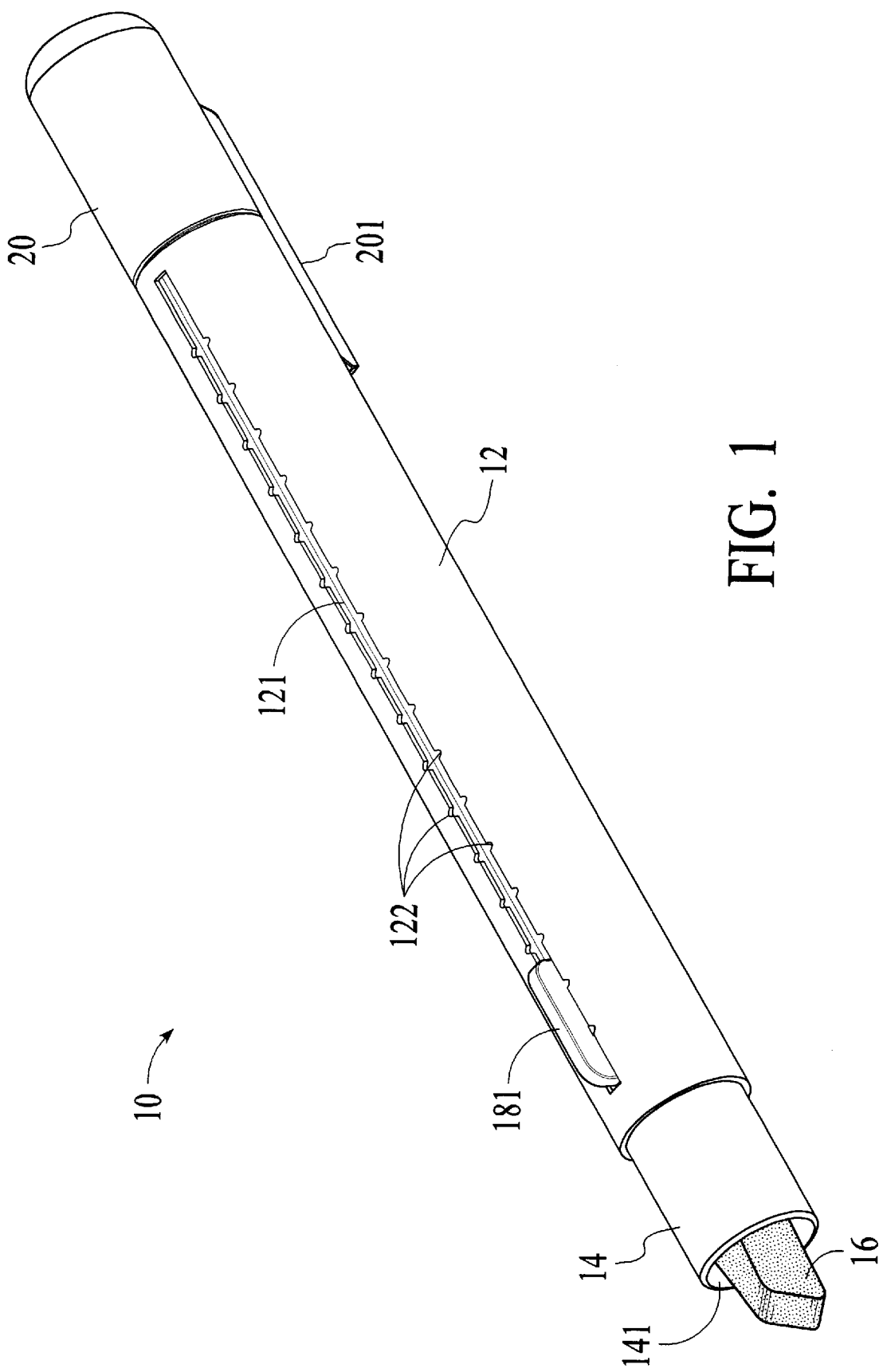
FIG. 1 is a perspective view of the advancing antiseptic marking pen of the present invention.
Figure 2:
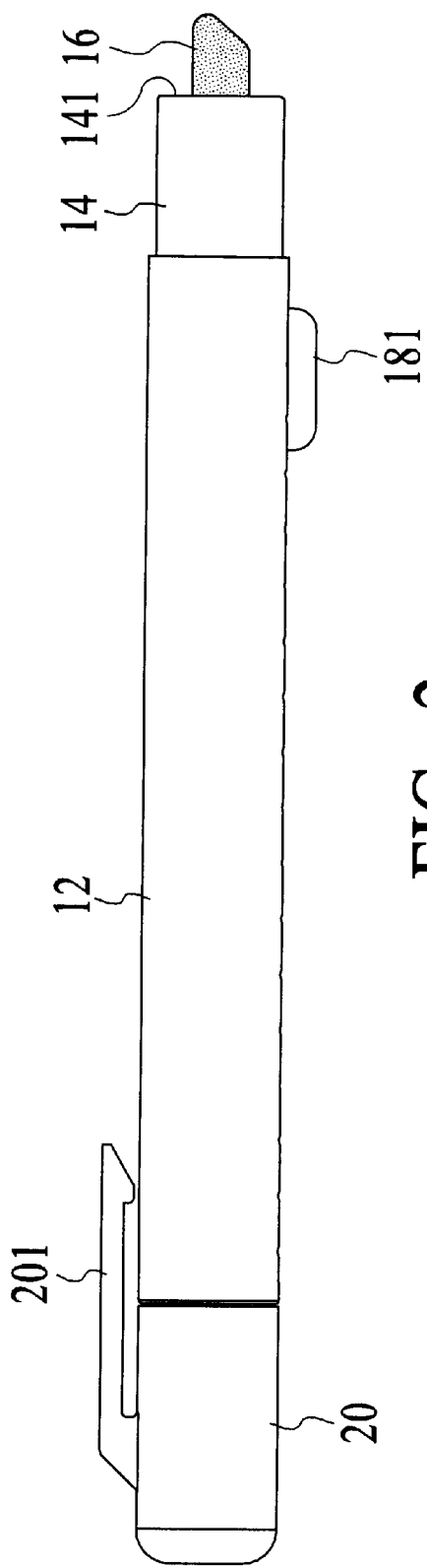
FIG. 2 is a side view of the pen.
Figure 3:
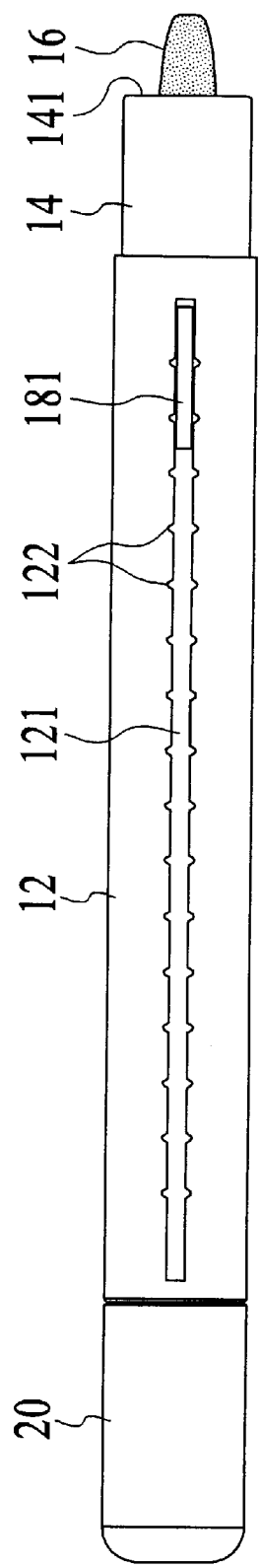
FIG. 3 is a rear view of the pen.

Referring first to FIGS. 1–3, the present invention is an advancing antiseptic marking pen 10. The marking pen 10 comprises chiefly an outer barrel 12 surrounding an inner sleeve 14. The sleeve 14 has an open end 141 and a closed end 142. A plurality of antiseptic/marking tips 16 are contained in an interior of the sleeve 14. An advancing mechanism 18 moves the tips 16 through the interior of the sleeve 14 to the open end 141 where the tips 16 are exposed for use, and then ejected. Unused tips 16 remain below the opening of the sleeve 14 to avoid contamination of the tips 16. When the marking pen 10 is not in use, a protective cap 20 covers the open end 141 of the inner sleeve 14 so that the tips 16 are not exposed to any external contaminants.

Figure 4:
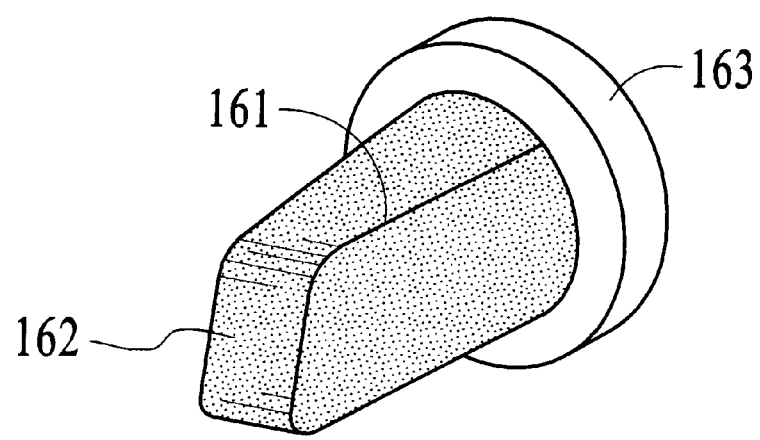
FIG. 4 is a detail perspective view of the antiseptic/marking tip of the pen.

Referring now chiefly to FIG. 4, the antiseptic/marking tips 16 comprise a main body 161, a tapered point 162, and a base 163. In the preferred embodiment, the antiseptic/marking tips 16 are formed from an absorbent material such as felt so that the tips 16 are able to retain the solution chosen for the cleansing and marking function. The base 163 of the tip 16 is shaped to conform to the interior of the inner sleeve 14. In the preferred embodiment, the base 163 is round, but as illustrated in the alternate embodiment shown in FIGS. 8 and 9, the base of the tip and the barrel of the pen can just as easily be triangular. It should be recognized that any shape desired by a user can be used for the base of the tip, the interior of the inner sleeve, and the barrel of the pen. The shape should be an ergonomically sound one, and should be comfortable to the user. In most cases, it is preferable if the cross sections of the tip base, the sleeve interior, and the barrel are all the same, but this is not strictly required.

Figure 5:
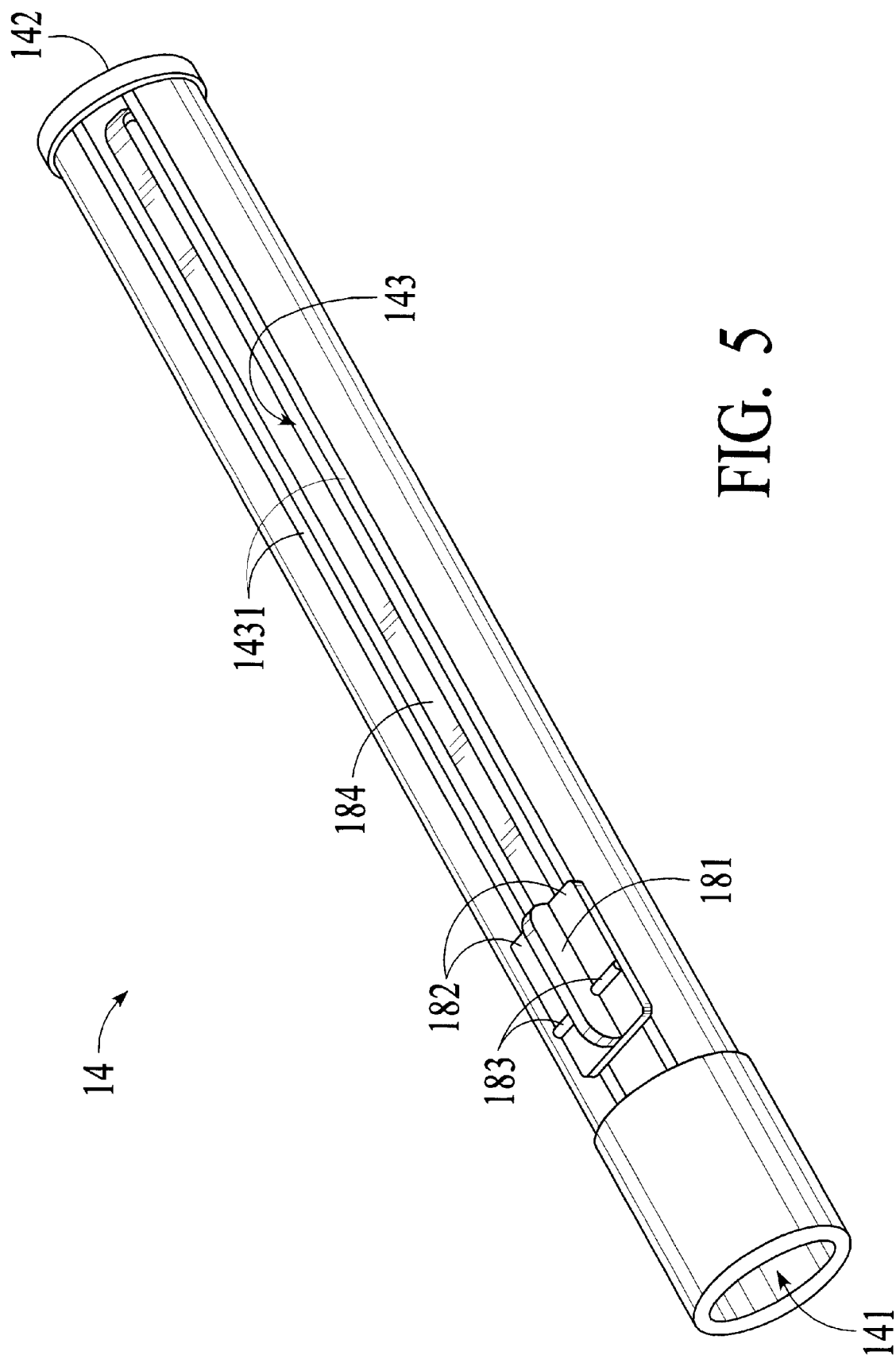
FIG. 5 is a perspective view of the inner sleeve of the pen.
Figure 6:
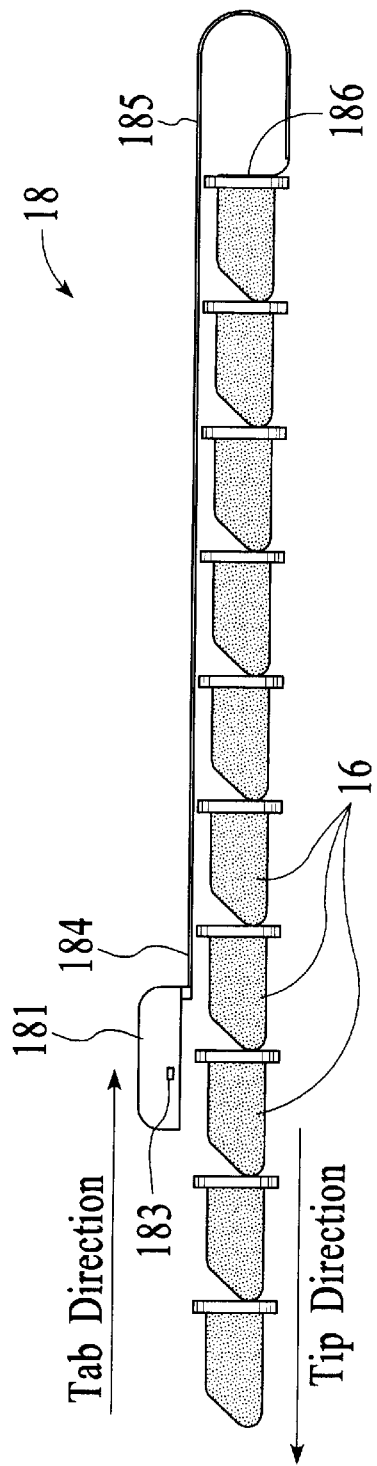
FIG. 6 is a side view of the tip stack and the flexible blade spring.
Figure 7:
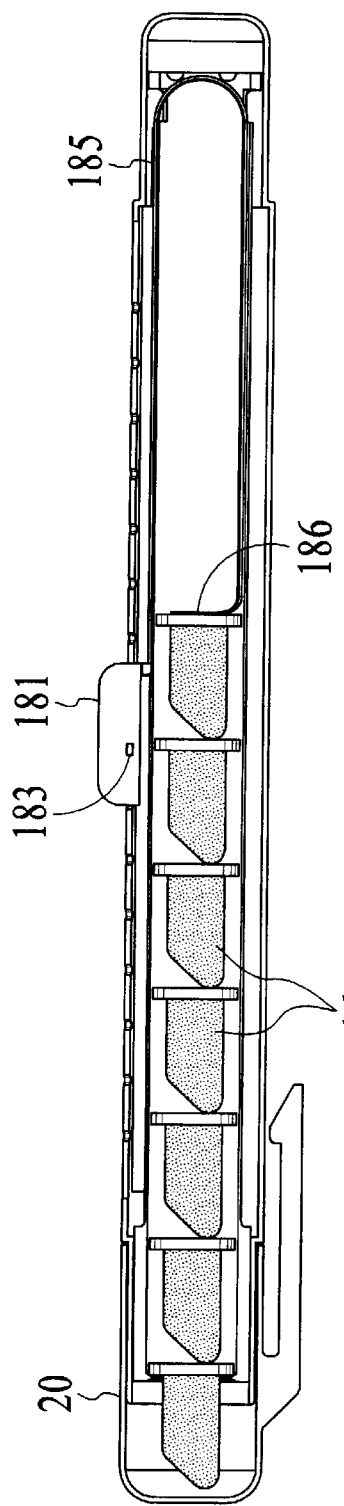
FIG. 7 is a side cutaway view of the assembled pen.

The antiseptic/marking tips 16 are loaded into the inner sleeve 14 (shown in FIG. 5) through the open end 141. The inner sleeve 14 has a longitudinal slot 143 on a top side. The sides 1431 of the slot 143 serve as guide rails for the advancing mechanism 18. The advancing mechanism 18 comprises an advancing tab 181 with a pair of protruding side wings 182 that rest on the guide rails 1431 of the slot 143. An elongated boss 183 protrudes from the upper surface of each of the side wings 182. A flexible blade spring 183 is attached to the advancing tab 181 and extends through the slot 143. The blade spring 184 is doubled onto itself behind the innermost tip 16 as is best illustrated in FIG. 6. This creates a doubled section 185 of the blade spring 184 that abuts the closed end 142 of the inner sleeve 14. A distal end of the blade spring 184 is bent to a 90° angle to provide a pushing surface 186 that contacts the base 163 of the innermost antiseptic/marking tip 16.

When the tips 16 and the advancing mechanism 18 have been assembled in the inner sleeve 14, the outer barrel 12 is attached. In the preferred embodiment, the outer barrel 12 is formed in two sections, and is then sonic welded around the inner sleeve 14. Clearly there are many methods of assembly known to those skilled in the art that will suffice to secure the barrel 12 around the inner sleeve 14 of the pen 10, thereby securing the tips 16 and the advancing mechanism 18 in the interior of the sleeve 14.

The outer barrel 12 includes a slot 121 correlating to the slot 143 on the inner sleeve 14. While coextensive in length with the inner sleeve slot 14, the outer barrel slot 121 is more narrow, needing only to accommodate travel of the upper end of the advancing tab 181. A plurality of transverse notches 122 lie along the length of the outer barrel slot 121. The notches 122 receive the bosses 183 on the side wings 182 of the advancing tab 181. A slight clearance must be left between the outer barrel 12 and the inner sleeve 14 so that the bosses 183 can move into and out of the notches 122. The inherent pressure of the doubled blade spring 184 urges the advancing tab 181 upward so that the bosses 183 remain secured in the notches 122 until pressure is applied to the advancing tab 181. While any number of notches 122 can be utilized in the outer barrel 12, it is recommended that the spacing between the notches be no more than one-half the length of the antiseptic/marking tips 16, so that at least two clicks of the advancing tab 181 are required to move the advancing mechanism 18 the length of a tip 16.

After assembly of the pen 10, a protective cap 20, typically with a pocket clip 201, is affixed to cover the open end 142 of the inner sleeve 14. The protective cap 20 forms an airtight seal over the open end 142 of the sleeve 14 so that the tips 16 cannot dry out when the pen is not in use. It should be noted that the cap 20 will snap on and form an airtight seal only after the antiseptic/marking tip 16 is ejected. The cap 20 will not fit if an antiseptic/marking tip 16 is exposed. This will alert the user that he failed to eject the used antiseptic/marking tip 16. Subsequent patients will therefore only be exposed to clean, unused antiseptic/marking tips 16, thereby avoiding cross contamination while reducing clean up time and effort.

First Alternate Embodiment

Figure 9:
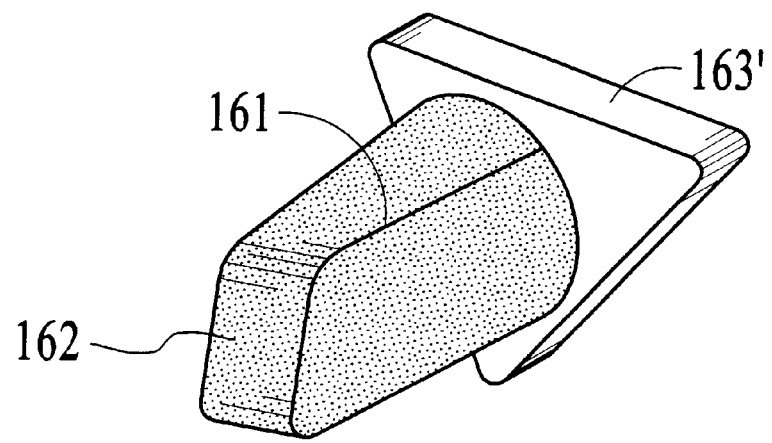
FIG. 9 is a detail perspective view of the antiseptic/marking tip of the triangular cross section embodiment of the pen.
Figure 8:
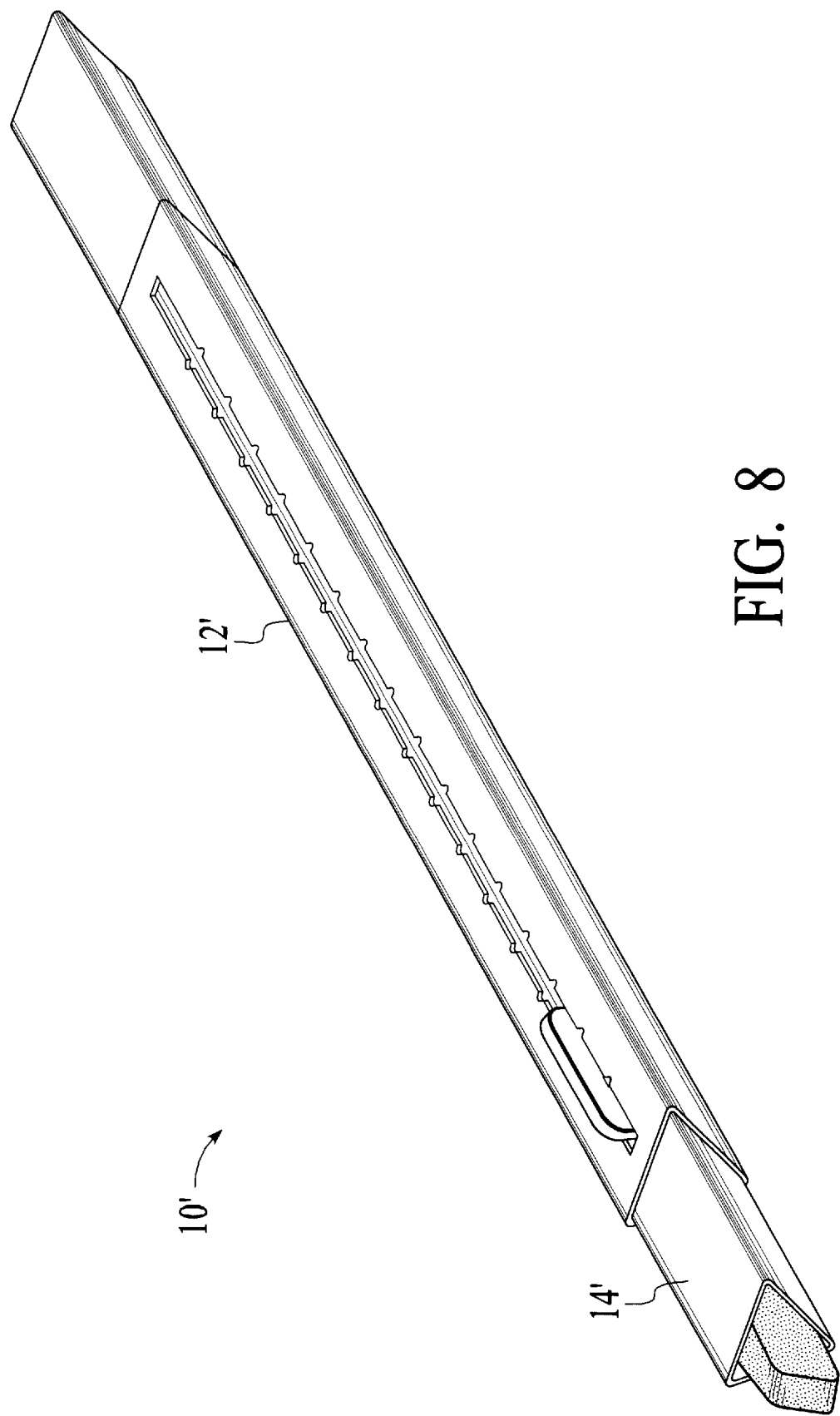
FIG. 8 is a perspective view of a triangular embodiment of the advancing antiseptic marking pen of the present invention.

FIGS. 8 and 9 illustrate an alternate embodiment of the advancing antiseptic marking pen 10'. In this embodiment, the invention is simply executed with a triangular outer barrel 12' and/or inner sleeve 14'. As illustrated in FIG. 9, the tips 16' can be made with a triangular base 163' so that they are more efficiently contained in a triangular inner sleeve 14'. The function and structure of the triangular pen 10' is in all other respects identical to that of the circular version of the marking pen 10.

Use of the advancing antiseptic marking pen 10 is as follows: The operator removes the protective cap 20 and places it on the closed end of the pen 10 for safekeeping. The operator then presses downward on the advancing tab 181 so that the bosses 183 are released from the notches 122. When the bosses 183 clear the notches 122, the advancing tab readily slides along the guide rails 143 formed by the sides of the slot 143 in the inner sleeve 14.

The operator slides the advancing tab 181 until the bosses 183 are secured in an adjacent (or succeeding) notch 122, and an antiseptic/marking tip 16 is exposed from the open end 141 of the inner sleeve 14 in an in-use position. After the indicated area on the patient is cleansed and simultaneously marked, the operator again depresses the advancing tab 181 to slide the advancing mechanism 18 further so as to eject the used marking tip 16. The protective cap 20 is then replaced by the operator over the open end 141 of the pen 10. The marking pen 10 can then be conveniently stored in the operator's pocket.

The above disclosure is not intended as limiting. Those skilled in the art will readily observe that numerous modifications and alterations of the device may be made while retaining the teachings of the invention. Accordingly, the above disclosure should be construed as limited only by the restrictions of the appended claims.

I claim:

1. An advancing antiseptic marking pen comprising:
   an outer barrel,
   an inner sleeve with an open end and a closed end,
   a plurality of antiseptic/marking tips that contain a colored antiseptic are contained in an interior of said sleeve, and
   an advancing mechanism; wherein
      said advancing mechanism creates a serial movement of said antiseptic/marking tips through said interior of said sleeve toward said open end of said sleeve to an in-use position in which an outermost one of said antiseptic/marking tips is exposed for use, and
      said serial movement moves said antiseptic/marking tips through said interior of said sleeve to eject said outermost one of said antiseptic/marking tips after it has been used.

2. The advancing antiseptic marking pen of claim 1, wherein said advancing mechanism comprises:
   an advancing tab with a pair of protruding side wings,
   a flexible blade spring attached to said advancing tab; wherein said advancing mechanism is installed in said inner sleeve, said inner sleeve having a longitudinal inner sleeve slot in one side thereof, said side wings of said advancing tab rest on sides of said inner sleeve slot, said sides of said inner sleeve slot serving as guide rails for said side wings of said advancing tab, and said outer barrel comprises an outer barrel slot, a top end of said advancing tab protrudes through said outer barrel slot, said advancing tab being contained in a space between said outer barrel and said inner sleeve; and wherein said blade spring extends through said interior of said inner sleeve and is doubled onto itself at said closed end of said inner sleeve behind an innermost one of said antiseptic/marking tips so as to create a doubled section of said blade spring that abuts said closed end of said inner sleeve, a distal end of said blade spring comprising a pushing surface that contacts said innermost one of said antiseptic/marking tips; such that said advancing mechanism advances said antiseptic/marking tips toward said open end of said inner sleeve when said advancing tab is pushed toward said closed end of said inner sleeve.

3. The advancing antiseptic marking pen of claim 2, wherein:

an elongated boss protrudes from an upper surface of each of said side wings, and a plurality of transverse notches lie along said outer barrel slot, said notches receive said bosses on said side wings of said advancing tab, a clearance being left between said outer barrel and said inner sleeve so that said bosses move into and out of said notches, inherent pressure of said blade spring urging said advancing tab upward so that said bosses are secured in said notches until pressure is applied to said advancing tab.

4. The advancing antiseptic marking pen of claim 3, wherein:

said transverse notches are spaced apart no more than one-half a length of said antiseptic/marking tips, so that said advancing tab must be moved through at least two notches to move said advancing mechanism the length of said tip.

5. The advancing antiseptic marking pen of claim 1, wherein:

a cross section of a base of said antiseptic/marking tips conforms to a cross section of said interior of said inner tube.

6. The advancing antiseptic marking pen of claim 5, wherein:

said base of said antiseptic/marking tips has a circular cross section.

7. The advancing antiseptic marking pen of claim 5, wherein:

said base of said antiseptic/marking tips has a triangular cross section.

8. The advancing antiseptic marking pen of claim 1, wherein:

a cross section of a base of said antiseptic/marking tips conforms to a cross section of said interior of said inner tube and to a cross section of said outer barrel.

9. The advancing antiseptic marking pen of claim 8, wherein:

said base of said antiseptic/marking tips has a circular cross section.

10. The advancing antiseptic marking pen of claim 8, wherein:

said base of said antiseptic/marking tips has a triangular cross section.

11. The advancing antiseptic marking pen of claim 1, wherein:

said antiseptic/marking tips comprise a main body, a tapered point, and a base, and said antiseptic/marking tips are formed at least in part of an absorbent material.

12. The advancing antiseptic marking pen of claim 1, wherein:

a protective cap covers said open end of said inner sleeve so as to form an airtight seal when said pen is not in use.

\* \* \* \* \*